United States Patent [19]

Korevaar

[11] Patent Number: 4,983,844

[45] Date of Patent: Jan. 8, 1991

[54] FAST ATOMIC LINE FILTER

[75] Inventor: Eric J. Korevaar, San Diego, Calif.

[73] Assignee: Thermo Electron Technologies Corp., San Diego, Calif.

[21] Appl. No.: 422,671

[22] Filed: Oct. 17, 1989

[51] Int. Cl.$^5$ .......................... G01J 5/00; G01J 5/08; G02B 5/20; G02B 5/22

[52] U.S. Cl. .................................. 250/382; 250/336.1

[58] Field of Search ......................... 250/382, 336.1

[56] References Cited

U.S. PATENT DOCUMENTS 4,024,396  5/1977  Hill et al. .................... 250/338.1
4,600,840  6/1986  Chutjian ....................... 250/338.5

OTHER PUBLICATIONS

Tatsuo Okada et al., "Sensitive Photon Detector Based on Solution Base Ionization", Optic Let., vol. 14, No. 18, Sep. 15, 1989.

*Primary Examiner*—Constantine Hannaher
*Assistant Examiner*—Jacob Eisenberg
*Attorney, Agent, or Firm*—John R. Ross

[57] ABSTRACT

A fast atomic line filter capable of operating at speeds and quantum efficiencies greatly in excess of prior art atomic line filters. Signal light excites to an intermediate energy level the atoms of a contained vapor. A pump beam further excited these atoms to a higher Rydberg level. Simultaneously the atoms are subjected to an electric field that Stark splits the Rydberg level and ionizes very quickly the doubly excited atoms. The resulting ions or electrons are then detected with near unity quantum efficiency by a detector sensitive to either ions or electrons. By directly detecting the resulting ions or electrons the fast atomic line filter has an inherently higher quantum efficiency and much greater speed than prior art ALF's which must use photosensitive detectors to detect fluorescence.

11 Claims, 1 Drawing Sheet

FAST ATOMIC LINE FILTER

This invention relates to optical filters and especially atomic line filters.

BACKGROUND OF THE INVENTION

The narrowest optical filter bandwidths are obtained with atomic line filters (ALF's) which have acceptance bandwidths on the order of 0.001 nm. In prior art, ALF's, broadband light containing narrowband signal light is passed through a color glass filter which cuts off wavelengths below a threshold value. The signal and remaining noise light enter an atomic vapor that only absorbs the signal light within the atom's 0.001 nm acceptance bandwidth thereby exciting those absorbing atoms to an intermediate energy level. A pump beam further excites these atoms to a second, higher energy level that then decays through various processes including fluorescence, to the ground state of the atom. The emitted fluorescence occurs at wavelengths below the threshold value. A second color glass filter then cuts off any wavelengths above the threshold which effectively permits passage of only the emitted narrowband fluorescence. In effect, the incoming signal has been internally shifted in wavelength by the atomic vapor, which then allows the use of two overlapping color glass filters to block any background radiation. For some applications these filters have two drawbacks, slow response time (about 500 ns for the alkali atoms) and low quantum efficiency which is defined as the ratio of the number of fluorescence photons detected to the the number of incoming signal photons. A need exists for a light filter that retains the acceptance bandwidth of an ALF but has a faster response time and higher quantum efficiency.

SUMMARY OF THE INVENTION

The present invention provides a fast atomic line filter capable of operating at speeds and quantum efficiencies greatly in excess of prior art atomic line filters. Signal light excites to an intermediate energy level the atoms of a contained vapor. A pump beam further excited these atoms to a higher Rydberg level. Simultaneously the atoms are subjected to an electric field that Stark splits the Rydberg level and ionizes very quickly the doubly excited atoms. The resulting ions or electrons are then detected with near unity quantum efficiency by a detector sensitive to either ions or electrons. By directly detecting the resulting ions or electrons the fast atomic line filter has an inherently higher quantum efficiency and much greater speed than prior art ALF's which must use photosensitive detectors to detect fluorescence.

DESCRIPTION OF PREFERRED EMBODIMENTS

Figure 1:
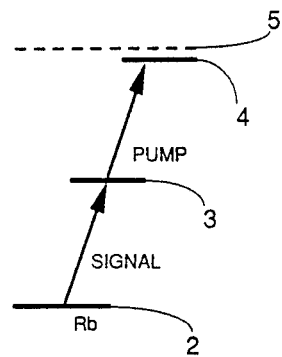
FIG. 1 is a general energy level diagram for the fast atomic line filter scheme.

An atomic line filter which has faster response time and higher quantum efficiency than prior art atomic line filters can be described by reference to the figures. FIG. 1 is a simplified energy level diagram for operation of a fast atomic line filter. In this case rubidium (Rb) was used as the active medium. The operation of the filter is based on the following sequence of events. A photon to be detected excites a Rb atom from the ground state 2 to an intermediate energy level 3. This atom is then further excited by a pump photon to a Rydberg level 4 Stark shifted by an applied electric field. The electric field then causes the atom to ionize in a time short compared to 1 ns. The filter can be designed for the detection of the resulting ion or electron.

Figure 2:
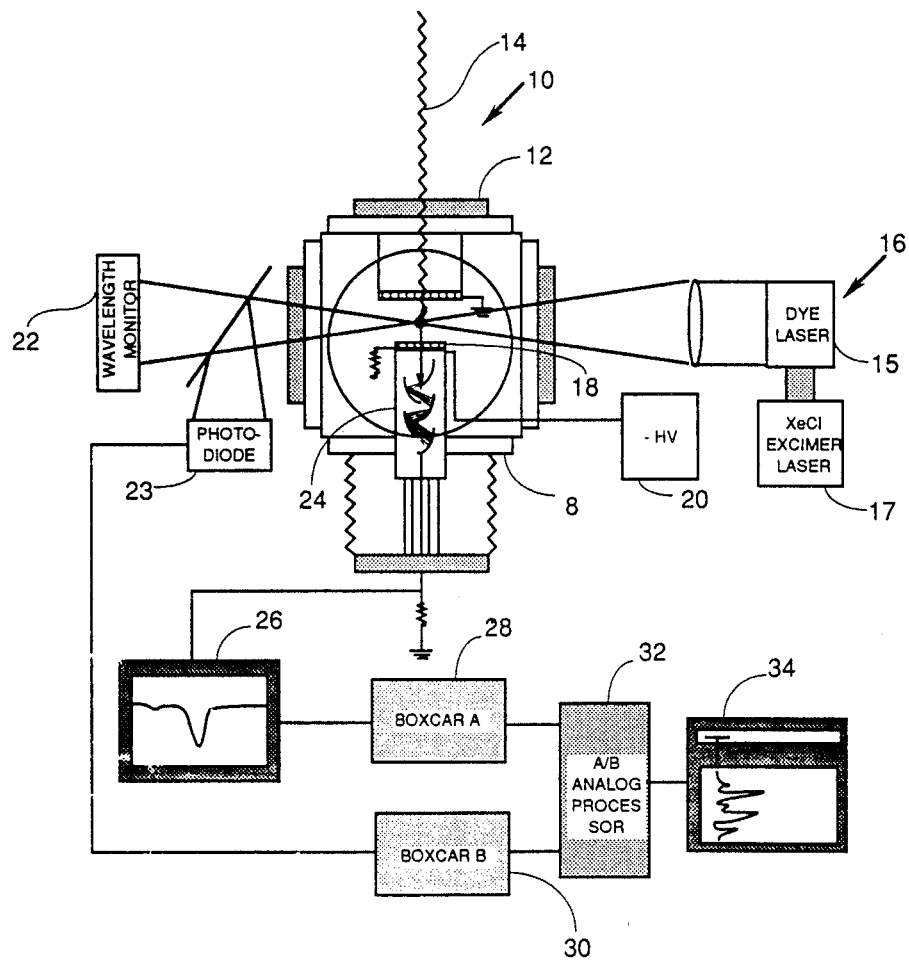
FIG. 2 is a schematic diagram showing the elements of the specific embodiment of the present invention.

A fast filter device is shown schematically in FIG. 2. A vacuum chamber 8 contains Rb vapor at a temperature of about 100° C. and pressure of about $10^{-4}$ torr. The chamber contains an aperture 10 covered by a color glass filter 12 chosen to cutoff wavelengths shorter than about 780 nm. Signal light at 780.03 nm (in our case produced by a diode laser 14) passes through filter 12. Photons from the signal light excite the Rb atoms to intermediate level 3 as shown in FIG. 1. Light from a pulsed narrowband ($<1$ GHz) dye laser pump 16 (comprised of excimer laser 17 and dye laser 15) further excites the Rb atoms from level 3 to a Rydberg level 4, also shown in FIG. 1, Stark shifted by a negative 2 kV potential applied to grid plate 18 by high voltage source 20. These atoms then ionize in a time short compared to 1 ns. Monitor 22 used to ensure that that pump laser is tuned to the correct wavelength and photodiode 23 measure the pump laser intensity. The resulting ions are accelerated toward grid plate 18 and then impact on the first dynode of electron multiplier 24 creating secondary electrons which are in turn multiplied by the subsequent stages of the electron multiplier. In effect about $10^6$ electrons are produced per single ion entering the multiplier providing a detectable signal at the output of the multiplier.

Oscilloscope 26 provides a real time picture of the multiplier voltage. The boxcar averagers 28 and 30, sample both the multiplier signal and the pump laser intensity. Their outputs are fed into analog processor 32, which divides the multiplier signal size by the pump laser intensity providing a normalized output signal and the result is displayed on chart recorder 34.

A feedback loop 36, is preferably provided to assure that the signal photons are precisely matched to the rubidium resonance absorption wavelength. The feedback loop consists of a beam splitter 38, a Rb absorption cell 40, and a photodiode monitor 42. A feedback control unit 44, is used to adjust the signal laser current (and therefore wavelength) such that the photodiode reads minimal signal pass through (maximum absorption by the Rb).

In an experimental setup the vacuum chamber was basically a cube with vacuum ports on each cube face. Sapphire windows were mounted on four sides of the cell; two for entry and exit of the pump laser, one for entry of the signal laser, and one for viewing the active region. The electron multiplier was made from a modified end-on photomultiplier tube. The photocathode and end window were removed and replaced by a stainless steel mesh, which served as the accelerating grid for the electron multiplier and as a field electrode to produce the ionizing electric field in the active region. The signal laser entry window was also covered with stainless steel mesh, providing the other electrode for the ionizing field. The ion multiplier was attached to the central cube via a vacuum feedthrough attached to a stainless steel bellows which allowed the electrode spacing to the varied from 0–1.0 cm. The remaining port had a high temperature resealable valve attached to it. Rb metal was loaded into the cell in an argon atmosphere and the cell was then sealed and removed from the vacuum system making a convenient self contained device. Rb vapor was produced by heating the cell with heater tapes wrapped around it and the entire device was wrapped in glass wool for uniform heat distribution. The signal and pump laser beams crossed perpendicularly in the active region of the cell. The field electrode on the signal laser entry window was held at ground and the field electrode on the end of the multiplier was held at high negative voltage. This provided a field that would accelerate ions into the electron multiplier. Ions hitting the first dynode produced secondary electrons that were then multiplied by subsequent dynodes which allowed the anode of the electron multiplier to be at ground potential.

The light exciting the $5s_{1/2}$–$5p_{3/2}$ transition was provided by a 15 mW diode laser nominally operating at 780 nm. The diode laser wavelength was locked to the $5s_{\frac{1}{2}}$–$5p_{3/2}$ transition by running a portion of the beam through a Rb reference cell held at 40° C. The diode laser was locked to the F=3, $^{85}$Rb line which has the highest cross section of the four peaks ($\sigma = 1.41 \times 10^{-11}$ cm$^2$, T=33° C.). The linewidth of the diode laser was about 30 MHz. The pump light exciting the transitions to the Stark split Rb Rydberg states was provided by a Littman[9] type grazing incidence dye laser using coumarin 480 ($5 \times 10^{-3}$ molar) dye, which in turn was pumped by a XeCl excimer laser running at a 10 Hz repetition rate. This provided light from the dye laser with a bandwidth of about 0.1 cm$^{-1}$, an energy of 10 $\mu$J/pulse, and a pulsewidth of about 10 ns. The dye laser could be continuously tuned from 475 nm to 492 nm using a rotatable feedback mirror. The mirror was driven by a piezoelectric controller so that resolutions of <0.001 nm in the dye laser wavelength were possible.

The signal laser had a 2 mm×2 mm cross sectional area and a power of 8 mW for the entire beam. The pump laser was focussed into the active region with a 30-cm focal length lens. This provided a beam waist of 100 $\mu$m at the intersection point of the two laser beams. The signal laser entry port was covered with a Schott RG-715 filter to block any short wavelength light that might produce photoelectrons. The pump ports were covered with a Schott BG-39 filter which blocked any UV from the XeCl laser from entering the cell. The cell was run at a temperature of 84° C. which corresponds to a Rb vapor density of about $10^{11}$ atoms/cm$^3$ or $3 \times 10^{-5}$ torr. The signal from the electron multiplier was fed into a boxcar averager as was the signal from the monitor photodiode of the pump laser. These were both fed into an analog signal processor so that the output signal of the multiplier was normalized with respect to the pump laser input power. The signal from the analog processor was recorded on a strip chart recorder, and the pump laser wavelength was continuously monitored with a high resolution spectrometer.

We were able to demonstrate with this experiment that the ionization cross section of the Stark split Rydberg state is enhanced by about 8.5 over the direct ionization cross section.

A preliminary estimate of the device quantum efficiency was obtained by reducing the signal laser power to a point at which single ion events were observed. The point at which single photons were obtained was when the signal was seen to go from zero to a particular value randomly in time with the on condition remaining constant in magnitude. This should then be the level of single ion counting. This allows us to scale for the number of ions produced when not in single ion counting mode for a given signal size on the oscilloscope. The measurements were performed at a temperature of 60° C. and using $\sigma = 1.41 \times 10^{-11}$ cm$^2$ (F=3 hyperfine peak of $^{85}$Rb) gives an optical absorption depth of 0.29 cm. The signal beam was apertured to 1 mm×1 mm size before entering the cell. The pump beam was located 2 mm from the signal beam entrance window and, assuming it was diffraction limited, has a waist of 100 $\mu$ at the intersection of the signal and pump beams. This leads to an active volume of $7.85 \times 10^{-6}$ cm$^3$ so that the number of atoms in the active region was $1.93 \times 10^4$ atoms. At 780 nm there are about $4 \times 10^{18}$ photons/sec/watt of signal beam. Correcting the signal for the 100 $\mu$ diameter of the pump beam leads to $4 \times 10^{17}$ photons/sec/watt. Then in 0.2 cm 50% of the incoming photons are absorbed leaving $2 \times 10^{17}$ that could reach the active region. The active region depth is only 100 $\mu$ and therefore only 4% of the incoming signal photons are absorbed giving $8 \times 10^{15}$ photons/sec/watt that are actually absorbed. The lifetime of the $5p_{3/2}$ state is 26 ns which gives $8 \times 10^{15}$ photons/sec/watt×26 ns but in equilibrium another factor of $\frac{2}{3}$ must be included due to the degeneracies of the excited states. Therefore there are $1.39 \times 10^8$ possible excited atoms/watt of incoming signal power available to promote to the Stark-shifted Rydberg state. Two different signal powers, 0.46 mW and 11.1 $\mu$W, were used to measure the number of output ions from the detector. These led to $2.1 \times 10^3$ ions and $1.11 \times 10^2$ ions respectively. According to the preceding calculations, there are $1.39 \times 10^8$ excited atoms available per signal watt, therefore if every excited atom were ionized we should see $6.39 \times 10^4$ and $1.54 \times 10^3$ ions produced respectively for the two input signal powers. This leads to quantum efficiencies of 3.2% and 7.2% respectively although this is only a crude measurement. The experimental apparatus is presently being modified to perform a more careful measurement.

While the above description describes specific embodiments of the present invention, the reader should not construe those as limitations on the scope of the invention but merely as example. In particular, for most applications the pump laser pulse length should be longer than that provided by the XeCl laser pumped dye laser in the present embodiment. A flashlamp pumped dye laser or a solid state laser will be appropriate for this requirements. For most applications, the Fast Atomic Line Filter itself should be constructed in a simple package (for instance out of glass) compatible with sockets such as those used for photomultiplier tubes. The pump laser light could be coupled in with fiber optics. Those skilled in the art will envision many other possible variations within its scope. For example the filter can be made to detect the electrons instead of ions of the ionized atom simply by changing the potential on the grid plate 18 to positive high voltage with maximum high voltage at the anode of the multiplier. The signal would then be a.c. coupled out of the device. The smaller mass of the electron would speed collection and therefore increase the speed of the device even more. Other gases such as lithium, potassium and cesium vapors can be used in the place of rubidium vapor with signal and pump beams chosen to correspond to the energy levels of the atoms of these vapors. A magnetic field applied parallel to the electric field would cause a Zeeman shift in the intermediate atomic energy level. Using this, one can in effect tune the fast atomic line filter to different signal wavelengths depending on the applied magnetic field. This could be used to detect Doppler shifts in a signal laser beam due to scattering off of moving aerosols. The amount of Doppler shifting could be measured by the fast ALF and the speed of the moving aerosol could then be calculated making a sensitive wind speed detector. Another application might be a gas detector whereby a laser beam is sent through a portion of atmosphere to be measured for a particular gas concentration. The gas could then Raman shift the frequency of the probe laser such that it falls into the absorption band of a particular fast ALF. The amount of Raman shifted light seen by the fast ALF would indicate the concentration of the gas, making the fast ALF useful for remote sensing. Both of these applications use the fast response time and high quantum efficiency of the fast ALF. Finally the electron multiplier might be replaced by a micro channel plate thereby giving the fast ALF an imaging capability.

Accordingly the reader should determine the scope of the invention by the appended claims and their legal equivalent and not by the examples which have been given.

I claim:

1. A fast atomic line filter system for detecting a narrowband signal light defining a nominal wavelength comprising:
   a first sealed chamber having an aperture for the passage of signal light into the interior of said container
   a gas contained in said sealed chamber, the atoms of said gas having a specific energy level corresponding to the nominal wavelength of said signal light and a Rydberg level,
   a pump means for exciting the atoms of said gas from said specific energy level to said Rydberg level.
   a high voltage means for creating an electrical potential across all or a portion of said gas said electrical potential being high enough to ionize essentially all atoms of said gas excited to said Rydberg level and a detection means for detecting ionization events.

2. A fast atomic line filter system as in claim 1 wherein said gas is chosen from a group consisting of lithium, sodium, potassium, rubidium and cesium.

3. A fast atomic line filter system as in claim 2 wherein said gas is rubidium.

4. A fast atomic line filter system as in claim 3 wherein said pump means comprises a laser device capable of producing a laser beam at about 480 nm.

5. A fast atomic line filter system as in claim 1 wherein said gas is potassium, and said pump means comprises a laser device capable of producing a laser beam at a wavelength of about 460 nm.

6. A fast atomic line filter system as in claim wherein said gas is cesium and said pump means is a laser device capable of producing a laser beam at a wavelength of about 1.07 $\mu$.

7. A fast atomic line filter system as in claim 1 and further comprising a signal means for producing said signal light.

8. A fast atomic line filter system as in claim 7 wherein said signal means comprises a sealed absorption cell containing the some gas as contained in said sealed chamber and a feedback circuit means for adjusting the wavelength of said signal light based on the portion of said signal light passing through said absorption cell.

9. A fast atomic line filter system as in claim 1 wherein said detector means for detecting ionization events comprises an electron detector.

10. A fast atomic line filter system as in claim 1 wherein said detector means for detecting ionization events comprises an ion detector.

11. A fast atomic line filter system as in claim 1 wherein said electron detector means comprises an electron multiplier.

* * * * *